United States Patent [19]

Bürstinghaus et al.

[11] Patent Number: 4,920,108
[45] Date of Patent: Apr. 24, 1990

[54] BISTHIOLPHOSPHATES AS PESTICIDES

[75] Inventors: Rainer Bürstinghaus, Heidelberg; Peter Hofmeister, Neustadt, both of Fed. Rep. of Germany

[73] Assignee: BASF Aktiengesellschaft, Ludwigshafen, Fed. Rep. of Germany

[21] Appl. No.: 149,111

[22] Filed: Jan. 27, 1988

[30] Foreign Application Priority Data

Feb. 11, 1987 [DE] Fed. Rep. of Germany ....... 3704123

[51] Int. Cl.$^5$ ...................... A01N 57/10; C07F 9/173
[52] U.S. Cl. ...................................... 514/134; 558/205
[58] Field of Search ........................ 558/205; 514/134

[56] References Cited

U.S. PATENT DOCUMENTS 3,662,034 5/1972 Oswald et al. ...................... 558/205
4,171,357 10/1979 Theobald et al. .................... 558/203
4,659,702 4/1987 Chaudarian et al. ............... 558/205

FOREIGN PATENT DOCUMENTS 1579592 11/1980 United Kingdom .

Primary Examiner—Anton H. Sutto
Attorney, Agent, or Firm—Keil & Weinkauf

[57] ABSTRACT

Bisthiophosphates of the general formula

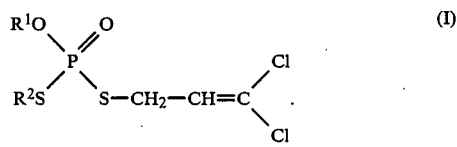

where $R^1$ is ethyl or isopropyl and $R^2$ is branched or straight-chain $C_1$–$C_4$-alkyl, and their use for combating pests.

7 Claims, No Drawings

BISTHIOLPHOSPHATES AS PESTICIDES

The present invention relates to novel bisthiolphosphates of the general formula I

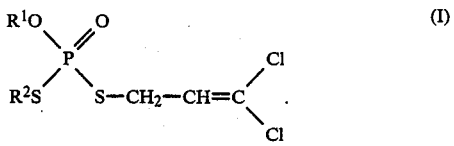

where $R^1$ is ethyl or isopropyl and $R^2$ is branched or straight-chain $C_1$-$C_4$-alkyl.

The invention further relates to pesticidal agents containing these bisthiolphosphates I as active ingredients, and a process for combating pests with these active ingredients.

Active ingredients from the group of chlorocyclopropyl-substituted dithiophosphoric acid esters are known for example from DE-A-26 34 587; they are suitable as insecticides and nematicides. However, their action, particularly at low concentrations, is not always fully satisfactory.

The object of the invention was therefore to provide novel bisthiolphosphates having an improved action.

$R^2$ in formula I has the following individual meanings: branched or straight-chain $C_1$-$C_4$-alkyl, such as methyl, ethyl, n-propyl, isopropyl, n-butyl, isobutyl, sec-butyl and tert-butyl, preferably methyl, ethyl, n-propyl, isopropyl, isobutyl and sec-butyl, and particularly preferably n-propyl, isobutyl and sec-butyl.

The novel compounds are prepared by reacting prior art 1,1-dichloro-3-halopropenes of the formula II

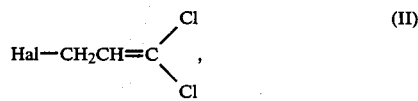

where Hal is fluorine, chlorine, bromine or iodine, with a salt of a corresponding dithiophosphoric acid derivative of the formula III

where Z is an alkali metal ion, e.g., lithium, sodium and potassium, one equivalent of an alkaline earth metal ion, e.g., calcium and magnesium, or an ammonium ion which is unsubstituted or substituted by one to four $C_1$-$C_{20}$-alkyl, preferably $C_1$-$C_8$-alkyl and particularly preferably $C_1$-$C_4$-alkyl, such as methyl, ethyl, n-propyl, isopropyl, n-butyl, isobutyl, sec-butyl and tert-butyl.

The reaction is carried out in the manner usual for the reaction of halogen compounds with alkali metal salts, e.g., from $-20°$ C. to 150° C., preferably 0° to 80° C., and particularly preferably from 20° to 60° C., in a solvent or diluent. If non-aqueous solvents are used, it may be advantageous to add a catalytic amount of potassium iodide or a complexing agent, e.g., a crown ether, to increase reactivity.

The compounds I according to the invention are obtained from the reaction mixture in the usual manner, e.g., by adding water and separating the phases, followed by distillation, and/or column chromatography.

Some of the novel compounds of the formula I are obtained in the form of colorless or weakly brownish oils, which can be freed from the remaining volatile constituents by fairly long heating under reduced pressure at moderately elevated temperature ("incipient distillation"), and purified in this manner.

The bisthiolphosphates of the formula I are suitable for effectively combating insect, mite and nematode pests. They may be used as pesticides in crop protection, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha,* and *Pieris brassicae;*

Examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chryocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;*

Examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletic pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina moristans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;*

Examples from the Heteroptera order are *Nezara viridula, Eurygaster integriceps, Blissus leucopterus, Dysdercus cignulatus, Dysdercus intermedius, Piesma quadrata,* and *Lygus pratenis;*

Examples from the Homoptera order are *Perkinsiella saccharicida, Nilaparvata lugens, Empoasca fabae, Psylla mali, Psylla piri, trialeurodes vaporariorum, Aphis fabae,*

*Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acrythosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;*

Examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blatella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance in the form of formulations or application forms prepared therefrom, for example directly sprayable solutions, powders, suspensions or dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene isophorone, etc., and strongly polar solvents such as dimethylformamide, dimethyl sulfoxide, N-methylpyrrolidone water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol ethers, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 1 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylne oxide and 1 mole of castor oil.

IV. 20 parts by weight of compound no. 2 is dissolved in a mixture consisting of 60 parts by weight of cyclohexanone, 30 parts by weight of isobutanol, 5 parts by weight of the adduct of 7 moles of ethylene oxide and 1 mole of isooctylphenol, 5 parts by weight of the adduct of 40 moles of ethylene oxide and 1 mole of castor oil.

V. 80 parts by weight of compound no. 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably from 0.5 to 90, wt% of active ingredient.

The active ingredient concentrations in the finished formulations may vary over a wide range. Generally, they are from 0.0001 and 10, and preferably from 0.01 to 1, %. The active ingredients may also successfully be used in the ultra-low-volume (ULV) method, where it is possible to apply formulations containing more than 95wt% of active ingredient, or even the active ingredient without additives.

In the open, the amount of active ingredient applied is from 0.001 to 10, and preferably from 0.01 to 2, kg/ha.

There may be added to the active ingredients (if desired, immediately before use (tankmix) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propion aldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5[4H]-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl($\pm$)-cis,trans-2,2-dimethyl-3-(2,2-dichlorovinyl)-cyclopropanecarboxylate, alpha-cyano-3-phenoxybenzyl($\pm$)-cis,trans-2,2-dimethyl-3-(2,2-dichlorovinyl)-cyclopropanecarboxylate, (s)-alpha-cyano-3-phenoxybenzyl-cis(1R,3R)-2,2-dimethyl-3-(2,2-dibromovinyl)-cyclopropanecarboxylate, 3,4,5,6-tetrahydrophthalimidoethyl-DL-cis,trans-chysanthemate, 2-methyl-5-(2-propynyl)-3-furylmethyl-chrysanthemate, and alpha-cyano-3-phenoxybenzyl-alpha-isopropyl-4-chlorophenylacetate.

MANUFACTURING EXAMPLE

O-ethyl-S-n-propyl-S-(3,3-dichloroprop-2-en-1-yl)-dithiophosphate

A mixture consisting of 21.4 g of potassium-O-ethyl-S-n-propyldithiophosphate, 90 ml of acetonitrile and 14.25 g of 1,1-dichloro-3-bromoprop-1-ene is heated at 50° C. for 8 hours. When the mixture has cooled, the solvent is removed under reduced pressure, the residue is taken up in methyl tertbutyl ether, and the mixture is washed three times with 5% strength sodium hydroxide solution and three times with water. The mixture is dried over sodium sulfate, the solvent is removed under reduced pressure and the residue is distilled at 0.01 bar/50° C. There is obtained 21.9 g (95%) of O-ethyl-S-n-propyl-S-(3,3-dichloroprop-2-en-1-yl)-dithiophosphate. $C_8H_{15}Cl_2O_2PS_2$ (309)

Calc.: C 31.0, H 4.8, Cl 23.0, Found: C 30.6, H 4.6, Cl 23.4.

The compounds I given in the table below may be obtained from corresponding precursors by the process according to the invention, and are expected to have a similar action.

The novel bisthiolphosphates of the formula I are characterized by the following infrared spectra with typical adsorption maximums from the fingerprint range between 1,500 cm$^{-1}$ and 900 cm$^{-1}$. Compounds without any physical data may be prepared in the same way and used as active ingredients.

TABLE

| Ex no. | R$^1$ | R$^2$ | Infrared absorptions [cm$^{-1}$] |
|---|---|---|---|
| 1 | C$_2$H$_5$ | n-C$_3$H$_7$ | |
| 2 | C$_2$H$_5$ | sec.-C$_4$H$_9$ | 1455, 1243, 1015, 953, 933 |
| 3 | C$_2$H$_5$ | iso-C$_4$H$_9$ | 1253, 1237, 1016, 954, 932 |
| 4 | C$_2$H$_5$ | iso-C$_3$H$_7$ | 1380, 1365, 1235, 1155, 1015, 950 |
| 5 | C$_2$H$_5$ | C$_2$H$_5$ | 1266, 1236, 1015, 955 |
| 6 | C$_2$H$_5$ | CH$_3$ | 1240, 1016, 954, 934 |
| 7 | C$_2$H$_5$ | t-C$_4$H$_9$ | |
| 8 | iso-C$_3$H$_7$ | C$_2$H$_5$ | 1375, 1266, 1237, 1099, 965 |
| 9 | iso-C$_3$H$_7$ | n-C$_3$H$_7$ | |
| 10 | iso-C$_3$H$_7$ | sec.-C$_4$H$_9$ | |
| 11 | iso-C$_3$H$_7$ | iso-C$_4$H$_9$ | |
| 12 | iso-C$_3$H$_7$ | CH$_3$ | |
| 13 | iso-C$_3$H$_7$ | C$_2$H$_5$ | |
| 14 | iso-C$_3$H$_7$ | n-C$_4$H$_9$ | |

USE EXAMPLES

The compounds according to the invention, or agents containing them, were compared with regard to their action on pests with the following art compounds:

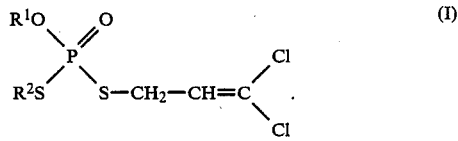

known from DE-A-26 34 587

| Comparative compound | known as compound no. | R |
|---|---|---|
| A | 5 | 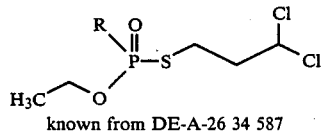 |
| B | 1 | H$_3$C―O― |
| C | 17 | H$_3$C―\―S― |

EXAMPLE A

Free-living nematodes; soil treatment 500 g of compost was intimately mixed with the active ingredients, and kept moist in pots for 10 days.

100 g samples were then removed, filled into gauze bags and placed in funnels to whose stem a hose was attached which was closed by means of a hose cock. The funnel was carefully filled with water until the bags were completely covered. After 24 hours, about 2 ml of water was removed at the cock and investigated as to the presence of nematodes.

| Compound no. 1 | 4 ppm | 100% kill |
|---|---|---|
| Compound no. 2 | 20 ppm | approx. 98% kill |
| Compound no. 3 | 40 ppm | 100% kill |
| Comparative agent A | 200 ppm | ineffective |
| Comparative agent B | 200 ppm | approx. 50% kill |

EXAMPLE B

*Blatta orientalis* (oriental cockroach); contact action

The bottoms of 1-liter glass jars was treated with acetonic solutions of the active ingredients.

After the solvent had evaporated, 5 adult cockroaches were placed in each jar.

The kill rate was determined after 48 hours.

| Compound no. 1 | 0.02 mg | 100% kill |
|---|---|---|
| | 0.1 mg | approx. 80% kill |
| Comparative agent B | 0.5 mg | 100% kill |

What we claim is:

1. Bisthiolphosphates of the formula I $$\begin{array}{c} R^1O \\ \diagdown \\ R^2S \end{array} \begin{array}{c} O \\ \diagup\!\!\!\diagup \\ P \\ \diagdown \\ S-CH_2-CH=C \end{array} \begin{array}{c} Cl \\ \diagdown \\ Cl \end{array} \quad (I)$$

where R$^1$ is ethyl or isopropyl and R$^2$ is branched or straight-chain C$_1$-C$_4$-alkyl.

2. Bisthiolphosphates of the formula I as set forth in claim 1, R$^1$ being ethyl or isopropyl and R$^2$ being n-propyl, isobutyl and sec-butyl.

3. A process for combating pests, wherein the pests and/or the areas and/or spaces to be kept free from pests are treated with a pesticidally effective amount of a bisthiolphosphate of the formula I as set forth in claim 1.

4. A pesticide containing a bisthiolphosphate of the formula I as set forth in claim 1 and conventional additives.

5. A pesticide as set forth in claim 4, containing from 0.1 to 95wt% of a bisthiolphosphate of the formula I.

6. A bisthiolphosphate of the formula I as set forth in claim 1, wherein R$^1$ is ethyl and R$^2$ is n-propyl.

7. A process for combatting pests, wherein the pests and/or the areas and/or spaces to be kept free from pests are treated with a pesticidally effective amount of a bisthiolphosphate of the formula I as set forth in claim 6.

* * * * *